(12) United States Patent
Hao et al.

(10) Patent No.: US 9,880,086 B2
(45) Date of Patent: Jan. 30, 2018

(54) NON-OVERLAPPING VISUALIZATION OF DATA RECORDS OF A SCATTER PLOT

(75) Inventors: Ming C. Hao, Palo Alto, CA (US); Umeshwar Dayal, Palo Alto, CA (US); Alex X. Zhang, San Jose, CA (US)

(73) Assignee: EntIT Software LLC, Sunnyvale, CA (US)

( * ) Notice: Subject to any disclaimer, the term of this patent is extended or adjusted under 35 U.S.C. 154(b) by 2708 days.

(21) Appl. No.: 12/290,322

(22) Filed: Oct. 28, 2008

(65) Prior Publication Data

US 2010/0103176 A1  Apr. 29, 2010

(51) Int. Cl.
*G06T 11/20* (2006.01)
*G01N 15/14* (2006.01)

(52) U.S. Cl.
CPC . *G01N 15/1475* (2013.01); *G01N 2015/1472* (2013.01)

(58) Field of Classification Search
CPC ... G06T 11/206; G06T 11/203; G06T 15/005; G06T 11/60; G06T 11/001
USPC ....... 345/418, 419, 420, 440, 443, 501, 581, 345/619
See application file for complete search history.

(56) References Cited

U.S. PATENT DOCUMENTS

| | | | |
|---|---|---|---|
| 3,487,308 A | 12/1969 | Johnson | |
| 5,581,797 A | 12/1996 | Baker | |
| 5,608,904 A | 3/1997 | Chaudhuri et al. | |
| 5,623,590 A | 4/1997 | Becker et al. | |
| 5,623,598 A | 4/1997 | Voigt et al. | |
| 5,634,133 A | 5/1997 | Kelley | |
| 5,659,768 A | 8/1997 | Forbes et al. | |
| 5,694,591 A | 12/1997 | Du et al. | |
| 5,757,356 A | 5/1998 | Takeasaki et al. | |
| 5,801,688 A | 9/1998 | Mead et al. | |
| 5,878,206 A | 3/1999 | Chen et al. | |
| 5,903,891 A | 5/1999 | Chen et al. | |
| 5,924,103 A | 7/1999 | Ahmed et al. | |
| 5,929,863 A | 7/1999 | Tabei et al. | |
| 5,940,839 A | 8/1999 | Chen et al. | |
| 5,986,673 A | 11/1999 | Martz | |
| 5,999,193 A | 12/1999 | Conley, Jr. et al. | |
| 6,052,890 A | 4/2000 | Malagrino, Jr. et al. | |
| 6,144,379 A | 11/2000 | Bertram et al. | |
| 6,188,403 B1* | 2/2001 | Sacerdoti et al. ............ 715/764 |

(Continued)

FOREIGN PATENT DOCUMENTS

EP  0778001  11/1996

OTHER PUBLICATIONS

M. Trutschl et al., "Intelligently Resolving Point Occlusion," Information Visualization, 2003, INFOVIS 2003, IEEE Symposium, Published Oct. 2003, Abstract only.

(Continued)

*Primary Examiner* — Xiao Wu
*Assistant Examiner* — Sarah Lhymn

(57) ABSTRACT

Non-overlapping visualization of data records of a scatter plot is provided by providing rows and columns in a visualization screen containing cells representing respective data records. The rows correspond to value ranges of a first attribute, and the columns correspond to value ranges of a second attribute. The value ranges are automatically generated for the rows and columns from data values of the data records.

24 Claims, 5 Drawing Sheets
(3 of 5 Drawing Sheet(s) Filed in Color)

(56) References Cited

U.S. PATENT DOCUMENTS

| | | | |
|---|---|---|---|
| 6,211,880 | B1 | 4/2001 | Impink, Jr. |
| 6,211,887 | B1 | 4/2001 | Meier et al. |
| 6,269,325 | B1 | 7/2001 | Lee et al. |
| 6,384,847 | B1 | 5/2002 | Rabenhorst |
| 6,400,366 | B1 | 6/2002 | Davies et al. |
| 6,429,868 | B1 | 8/2002 | Dehner, Jr. et al. |
| 6,466,946 | B1 | 10/2002 | Mishra et al. |
| 6,502,091 | B1 | 12/2002 | Chundi et al. |
| 6,584,433 | B1 | 6/2003 | Zhang et al. |
| 6,590,577 | B1 | 7/2003 | Yonts |
| 6,603,477 | B1 | 8/2003 | Tittle |
| 6,658,358 | B2 | 12/2003 | Hao et al. |
| 6,684,206 | B2 | 1/2004 | Chen et al. |
| 6,727,926 | B1 | 4/2004 | Utsuki et al. |
| 6,934,578 | B2 | 8/2005 | Ramseth |
| 7,020,869 | B2 | 3/2006 | Abrari et al. |
| 7,202,868 | B2 | 4/2007 | Hao |
| 7,221,474 | B2 | 5/2007 | Hao et al. |
| 7,313,533 | B2 | 12/2007 | Chang et al. |
| 7,567,250 | B2 | 7/2009 | Hao et al. |
| 7,714,876 | B1 | 5/2010 | Hao |
| 7,800,613 | B2* | 9/2010 | Hanrahan et al. ............ 345/440 |
| 7,844,926 | B1* | 11/2010 | Russell .......................... 716/106 |
| 7,924,283 | B1 | 4/2011 | Hao |
| 2002/0118193 | A1 | 8/2002 | Halstead, Jr. |
| 2003/0030637 | A1* | 2/2003 | Grinstein et al. ............. 345/420 |
| 2003/0065546 | A1 | 4/2003 | Goruer et al. |
| 2003/0071815 | A1 | 4/2003 | Hao et al. |
| 2003/0128212 | A1 | 7/2003 | Pitkow |
| 2003/0221005 | A1 | 11/2003 | Betge-Brezetz et al. |
| 2004/0051721 | A1 | 3/2004 | Ramseth |
| 2004/0054294 | A1 | 3/2004 | Ramseth |
| 2004/0054295 | A1 | 3/2004 | Ramseth |
| 2004/0095349 | A1 | 5/2004 | Bito et al. |
| 2004/0183799 | A1 | 9/2004 | Hao et al. |
| 2004/0201588 | A1 | 10/2004 | Meanor |
| 2004/0210540 | A1 | 10/2004 | Israel et al. |
| 2005/0066026 | A1 | 3/2005 | Chen et al. |
| 2005/0119932 | A1 | 6/2005 | Hao |
| 2005/0219262 | A1 | 10/2005 | Hao et al. |
| 2006/0095858 | A1 | 5/2006 | Hao et al. |
| 2006/0221077 | A1* | 10/2006 | Wright et al. ................ 345/428 |
| 2007/0225986 | A1 | 9/2007 | Bowe, Jr. et al. |
| 2008/0033790 | A1* | 2/2008 | Nickerson et al. ............. 705/10 |
| 2009/0033664 | A1 | 2/2009 | Hao et al. |

OTHER PUBLICATIONS

T. Buring et al., "User Interaction with Scatterplots on Small Screens—A Comparative Evaluation of Geometric-Semantic Zoom and Fisheye Distortion," Visualization and Computer Graphics, IEEE Transactions, Published Sep.-Oct. 2006, pp. 1-8.

Deun et al., Multidimensional Scaling, Open and Distance Learning, Jan. 12, 2000 (pp. 1-16).

http://www.pavis.org/essay/multidimensional_scaling.html, 2001 Wojciech Basalaj, (pp. 1-30).

D. Keim et al Pixel Bar Charts: A New Technique for Visualization Large Multi-Attribute Data Sets with Aggregation:, HP Technical Report, Apr. 2001, pp. 1-10.

M. Ankerst et al "Towards an effective cooperation of the computer and the computer user for classification, Proc. 6th Int. Conf. on Knowledge Discovery and Data Mining ," (KDD'2000), Aug. 20-23, 2000, Boston, MA, 2000, pp. 1-10.

M.C. Hao et al "Visual Mining of E-customer Behavior Using Pixel Bar Charts,", HP Technical Report, Jun. 20, 2001, pp. 1-7.

B. Shneiderman, "Tree Visualization with Treemaps: a 2-D Space-Filling Approach", pp. 1-10, Jun. 1991.

Daniel Keim et al "Designing Pixel-Orientated Visualization Techniques: Theory and Applications" IEEE Transactions on Visualization and Computer Graphics, vol. 6, No. 1, Jan.-Mar. 2000, pp. 59-78.

Jessica Lin, Eamonn Keogh, Stefano Lonardi, Jeffrey P. Lankford, Donna M. Nystrom; Visually Mining and Monitoring Massive Time Series; 2004; International Conference on Knowledge Discovery and Data Mining archive, Proceedings of the tenth ACM SIGKDD international conference on Knowledge discovery and data mining table of contents; pp. 460-469.

Eamonn Keogh, Harry Hochheiser, and Ben Shneiderman; An Augmented Visual Query Mechanism for Finding Patterns in Time Series Data; 2002; Lecture Notes in Computer Science, Proceedings of the 5th International Conference on Flexible Query Answering Systems; Springer-Verlag; vol. 252212002; pp. 240-250.

Chris Stolte et al., "Polaris: A System for Query, Analysis and Visualiztion of Multidimensional Relational Databases," IEEE Transactions on Visualization and ComputerGraphics, vol. 8, No. 1, pp. 1-14 (Jan.-Mar. 2002).

Daniel A. Keim et al., "VisDB: Database Exploration Using Multidimensional Visualization," IEEE Graphics and Applications, vol. 14, No. 5, pp. 40-49 (1994).

Matthew O. Ward, "XmdvTool: Integrating Multiple Methods for Visualizing Multivariate Data," Proc. Visualization, pp. 326-331 (Oct. 1994).

H. Hochheiser et al., "Dynamic Query Tools for Time Series Data Sets: Timebox Widgets for Interactive Exploration," Information Visualization, vol. 3, pp. 1-18 (2004.

P. Buono et al., "Technical Research Report, Interactive Pattern Search in Time Series," Institute for Systems Research, TR 2005-57, pp. 1-11 (2004.

J. Yang et al., "Visual Hierarchical Dimension Reduction for Exploration of High Dimensional Datasets," Joint Eurographics/IEEE TCVG Symposium on Visualization, pp. 19-28 (May 2003).

J. Fekete et al., "Interactive Information Visualization of a Million Items," Information Visualization, 2002, INFOVIS 2002, IEEE Symposium, Published Oct. 2002, pp. 1-8.

UCLA Academic Technology Services, Stat Computing, SPSS FAQ—How do I interpret the results from crosstabs? dated at least as early as Sep. 2008 (2 pages).

* cited by examiner

NON-OVERLAPPING VISUALIZATION OF DATA RECORDS OF A SCATTER PLOT

BACKGROUND

Traditional scatter plots have been widely used to display correlation or association between two variables. A scatter plot is a chart that uses Cartesian coordinates (e.g., x-axis or y-axis coordinates) to display values for the two variables. The data displayed in the scatter plot is a collection of points, each having one coordinate on the horizontal axis and one on the vertical axis. An example of a scatter plot is depicted in FIG. 1, where the horizontal axis variable represented in the example of FIG. 1 is CPU busy (a percentage value), and the vertical axis corresponds to Queue length. CPU busy in the example represents the percentage of time that the CPU is busy, while Queue length represents a length of a queue of jobs waiting for execution by the CPU.

Various points are plotted in the scatter plot of FIG. 1, where the data points correspond to a particular pair of CPU busy value and Queue length value. A first section 100 of the scatter plot represents the correlation between Queue length values and CPU busy values from 0 to about 70%. As indicated in the example of FIG. 1, the Queue length values for data records in the first section 100 are relatively low (50 or below). On the other hand, a second section 102 of the scatter plot depicted in FIG. 1 shows higher values of Queue length associated with higher CPU busy values. The section 102 is considered to contain "exceptional" points, which are data points that represent excessive CPU busy values (e.g., ≥98%) and large Queue lengths (e.g., ≥300).

From the scatter plot of FIG. 1, a viewer may assume that there are not many data points in the section 100 of the scatter plot. Such an assumption may be incorrect, as there in fact may be a large number of data points in the section 100, but the presence of such a large number of data points may be obscured due to overlapping (overlay of) data points (e.g., many data points sharing the same or very similar Queue length and CPU busy values). As a result, a traditional scatter plot can show just a relatively small number of distinct data points, even though there may be a much larger number of data points that the viewer cannot see as a result of overlapping. Such overlapping of data points can hide the true extent of the relationship between different variables in a traditional scatter plot.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are described, by way of example, with respect to the following figures.

DETAILED DESCRIPTION

Figure 1:
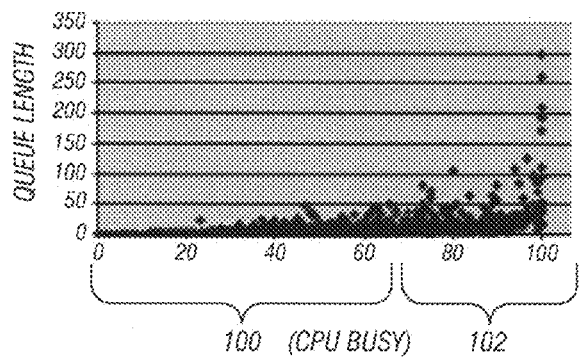
FIG. 1 illustrates a conventional scatter plot that depicts the relationship between two variables.

In accordance with some embodiments, a visualization technique or mechanism is provided to allow for representation of data records of a scatter plot without overlapping of data records (non-overlapping visualization of the data records). The visualization technique or mechanism provides a visualization screen that has rows and columns containing cells representing respective data records of the scatter plot. The rows correspond to value ranges of a first attribute of the data records, and the columns correspond to value ranges of a second, different attribute of the data records. The value ranges for the rows and columns can be automatically generated from incoming data of the data records. A "value range" of an attribute refers to a range of values of the attribute, where the values can be numerical values. Also, the cells can be ordered according to a third attribute. Ordering the cells refers to arranging the cells according to values of an ordering attribute (such as arranging cells from left to right and/or from bottom to top according to the values of the ordering attribute).

The cells can have the same size or different sizes.

In addition, colors (or other visual indicators) can be assigned to the cells according to values of a fourth attribute. An example of another visual indicator includes different patterns. Effectively, the visualization screen according to some embodiments provides for a multi-dimensional representation of the data records, including a first dimension corresponding to the first attribute, a second dimension corresponding to the second attribute, a third dimension corresponding to the third attribute, and a fourth dimension corresponding to the fourth attribute.

As used here, the term "scatter plot" refers to either a traditional scatter plot or a scatter plot represented with a visualization screen according to some embodiments. A traditional scatter plot uses Cartesian coordinates (e.g., a horizontal or x-axis and a vertical or y-axis), with data points plotted against the values of the variables in the Cartesian coordinate system to provide the scatter plot. On the other hand, a scatter plot that is represented by a visualization screen according to some embodiments refers to a representation of data records in rows and columns that have cells that represent respective data records.

In some embodiments, each row of cells runs generally in a horizontal direction of the visualization screen, while each column of cells runs generally in a vertical direction of the visualization screen. In such embodiments, each row is confined between a corresponding first horizontal line and corresponding second horizontal line spaced apart from the first horizontal line. In this manner, the rows do not intrude into neighboring rows—in other words, each of the rows does not intrude into neighboring rows. Similarly, in such embodiments, each column is confined between a corresponding first vertical line and corresponding second vertical line, such that each of the columns does not intrude into neighboring columns.

The arrangement of rows and columns of cells defines a regular array of blocks of cells, where each block is at the intersection of a corresponding row and column. A "regular array" of blocks means that within each particular row, the blocks of the particular rows are of equal height, and within each particular column, the blocks of the particular column have equal width. Note, however, that the blocks in different rows can have different heights (due to different value ranges of the first attribute), and the blocks in different columns can have different widths (due to different value ranges of the second attribute).

Figure 2:
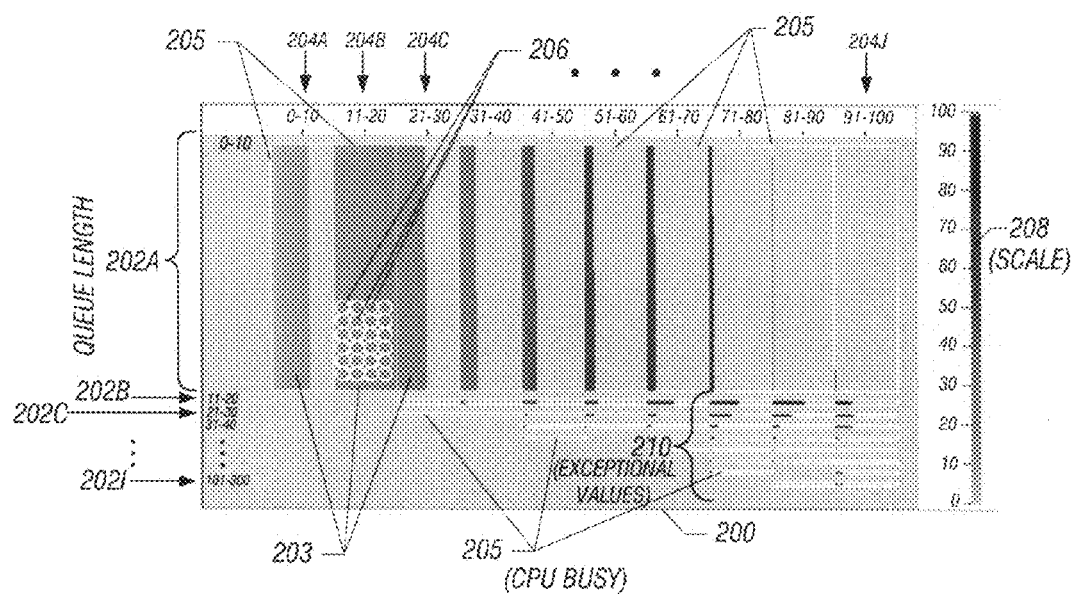
FIG. 2 illustrates a visualization screen that has rows and columns containing cells representing respective data records of a scatter plot, in accordance with an embodiment.

FIG. 2 shows a visualization screen 200 that provides visualization of data records of a scatter plot, where the data records in the example are the same data records as those depicted in the scatter plot of FIG. 1. By using the visualization screen 200 of FIG. 2, overlay of (overlapping) data points that can be present in a traditional scatter plot (FIG. 1) can be avoided. The visualization screen 200 has rows 202A, 202B, 202C, . . . , 202I (collectively referred to as "rows 202") that represent corresponding Queue length (first attribute) value ranges (e.g., 0-10, 11-20, 21-30, 31-40, . . . , 101-300) in the example.

The visualization screen 200 also includes columns 204A, 204B, . . . , 204J (collectively referred to as "columns 204") that correspond to value ranges of the CPU busy attribute (second attribute) (e.g., 0-10, 11-20, 21-30, 31-40, and so forth). The intersections of the rows 202 and columns 204 define corresponding blocks 205.

Cells 206 are schematically illustrated as enlarged circles in the block 205 in column 204B of row 202A. The cells 206 represent respective data records. Note that the cells 206 are enlarged in the diagram to allow for ease of viewing in FIG. 2. In actuality, the cells are smaller in size, and do not have to be circular. The cells 206 are assigned respective colors based on values of a coloring attribute, which in this example is also CPU busy. A scale 208 indicates the mapping of colors to different values of CPU busy. Similar cells are provided in the other blocks defined by intersections of rows 202 and columns 204.

In the example of FIG. 2, columns 204A, 204B in rows 202B, 202C, . . . , 202I are empty (in other words, columns 204A, 204B do not contain any cells in any of rows 202B, 202C, . . . , 202I). This is because with CPU busy having low values (0-10 and 11-20 for columns 204A, 204B, respectively), it is unlikely for any data records to be associated with Queue lengths having a value greater than 10. Similarly, as illustrated in the example of FIG. 2, blocks at intersections of other rows and columns are also empty.

In row 202B, note that as the CPU busy values increase (in columns 204C and forward), the number of data records appearing in these successive columns increase. This is due to the fact that as CPU busy values increase (indicating that loading on the CPU becomes heavier), the queue length also increases (indicating that the number of jobs waiting for execution is increasing). This pattern is also present in the other combinations of rows and columns.

Note that a section 210 of the visualization screen 200 corresponds to the section 102 of FIG. 1. In FIG. 2, the number of data records contained in section 210 of visualization screen 200 is relatively small, compared to the number of records found in row 202A in columns 204A, 204B, 204C, etc.

What is depicted in FIG. 2 is thus contrary with what would be expected from viewing just the traditional scatter plot of FIG. 1. From the conventional scatter plot of FIG. 1, a viewer would expect that there are relatively low numbers of data records for low Queue length values and low CPU busy values (lower left portion of the scatter plot of FIG. 1). However, the relatively low number of data records appearing in the lower left portion of the scatter plot of FIG. 1 is due to overlapping of data records such that the true number of data records in this portion of the scatter plot of FIG. 1 is obscured.

On the other hand, with the visualization screen 200 of FIG. 2, overlapping of data records is avoided such that a viewer can see the true extent of the number of records for different combinations of CPU busy and Queue length values. Effectively, the visualization screen 200 reveals data records in the conventional scatter plot that have been obscured due to overlays.

Generally, to allow for distinct data points associated with a scatter plot to be viewed in the visualization screen 200, first value groups and second value groups are defined to represent the horizontal axis and vertical axis values of a scatter plot. The first value groups define corresponding columns 204 in FIG. 2, and the second value groups define corresponding rows 202 in FIG. 2. Also, a set of cells are defined for representing data records within each of the blocks defined by the rows and columns. The cells are used to fill in the blocks. Moreover, a set of colors can be assigned to represent values of the data records represented by the cells. In addition, the cells can be ordered according to at least one attribute within each block (such as from left to right and from bottom to top).

A further feature provided by some embodiments is that user interaction is enabled such that a user can perform zooming or other actions to view portions of a scatter plot or to perform other interactions in the visualization screen.

Figure 3:
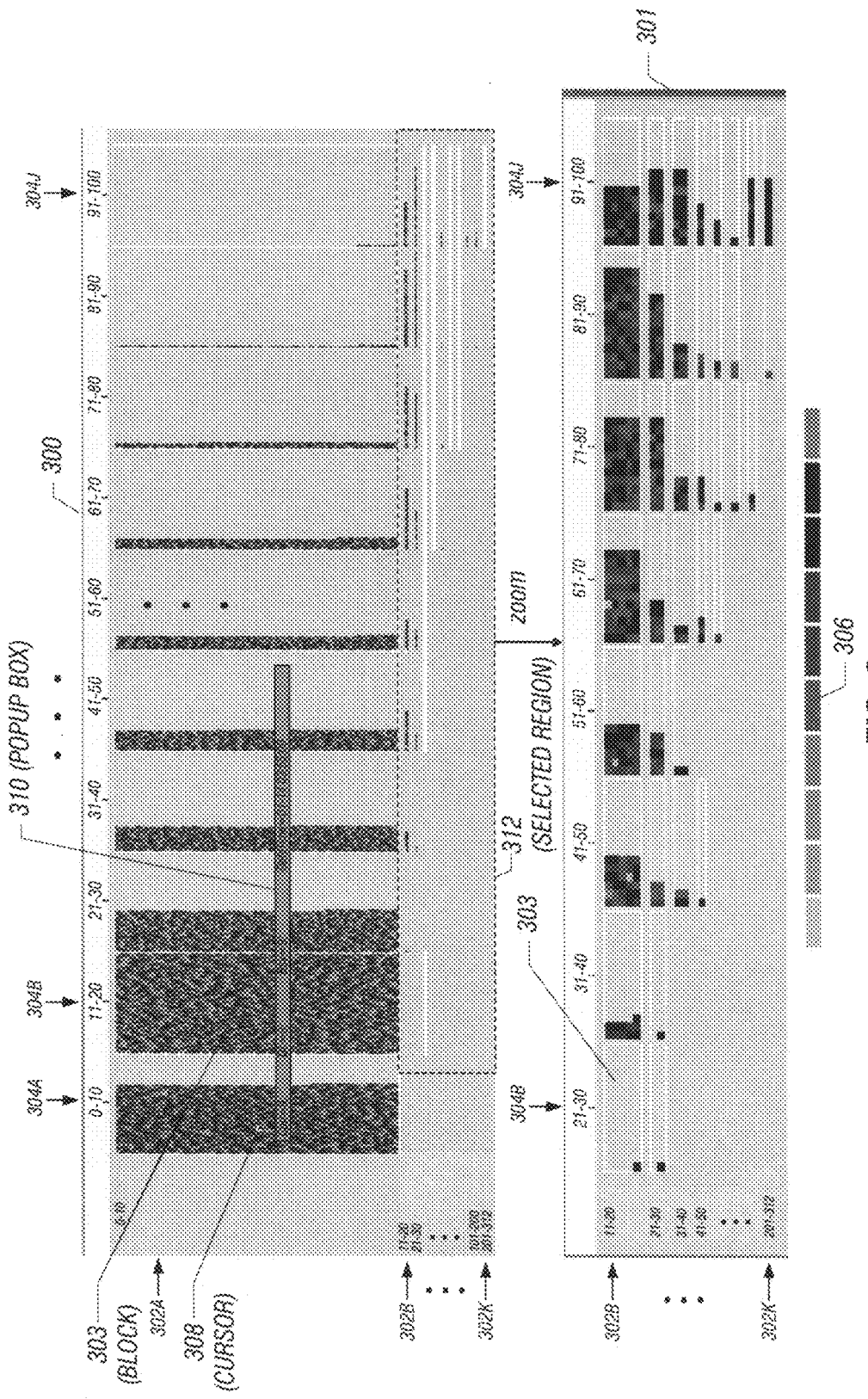
FIG. 3 depicts a visualization screen having rows and columns containing cells representing respective data records of a scatter plot, in accordance with another embodiment.

Note that in FIG. 2, the color assigned to each respective cell is based on the value of CPU busy, which is also the attribute for defining the various numerical ranges corresponding to the rows 204 of FIG. 2. In a different implementation, the color assigned to each cell can be based on a different attribute, as depicted in a visualization screen 300 illustrated in FIG. 3. In the example of FIG. 3, columns 304A, 304B, . . . , 304J represent corresponding value ranges for the attribute CPU busy, while rows 302A, 302B, . . . , 302K represent corresponding value ranges for the Queue length attribute. Blocks 303 at the intersection of the columns and rows of the visualization screen 300 are filled (partially or fully) with cells, where each cell represents a data record. In a block 303 that is the intersection of a row and column, cells are ordered based on the value of a selected attribute, which in the case of FIG. 3 is the date/time attribute. The color of each cell can represent the value of a corresponding coloring attribute, such as CPU number in the FIG. 3 example. As depicted in a scale 306 on the bottom of FIG. 3, different CPU numbers are assigned to different colors. In the visualization screen 300 of FIG. 3, a cell having a first color will correspond to a first CPU number, a cell having a second color will correspond to a second CPU number, and so forth.

As further depicted in FIG. 3, a cursor 308 can be moved over any particular cell in the visualization screen 300, which will cause a popup box 310 to depict information relating to the particular cell (e.g., CPU number, Queue length value, CPU busy value, date/time, etc.).

As further depicted in FIG. 3, a user can perform some type of an interaction in the visualization screen 300, such as a rubber-band action (in which the user selects, using an input device such as a mouse, keyboard, etc.) a region 312 in the visualization screen 300 that is of interest). Selecting the region 312 of interest causes another visualization screen 301 to be displayed, in which rows 302B, 302C, . . . , 302K are shown, along with columns 304B, 304C, . . . , 304J. Note that in the visualization screen 301, column 304A and row 302A of visualization screen 300 are not shown. Selecting the region 312, which is less than the entire visualization screen 300, effectively causes visualization software to zoom into the region of interest, such that the blocks 303 in the visualization screen 301 can be viewed more closely (cells are shown to be larger than cells of visualization screen 300).

Figure 4:
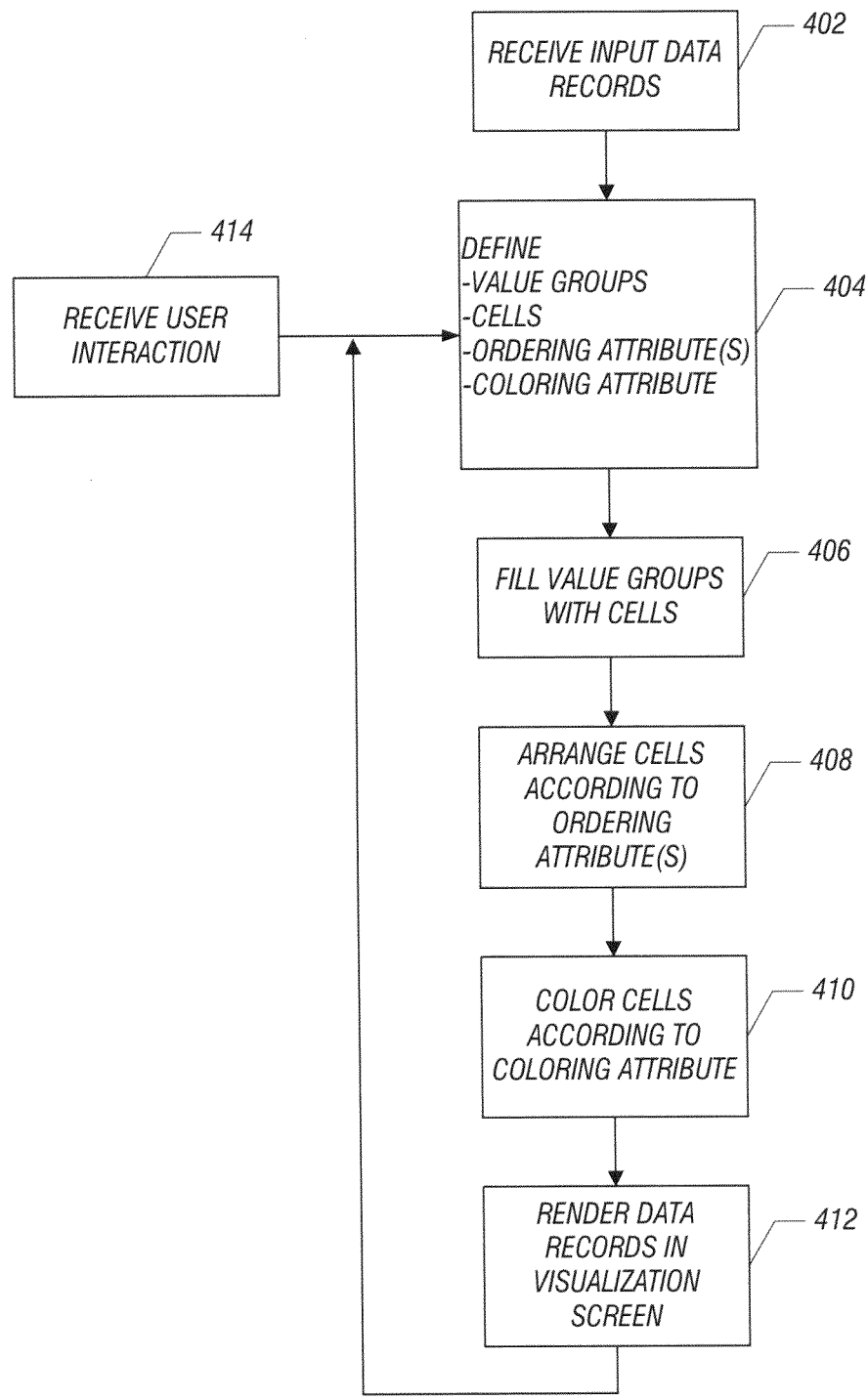
FIG. 4 is a flow diagram of a process of visualizing data records of a scatter plot, according to an embodiment.

FIG. 4 is a flow diagram of a process of visualizing data records of a scatter plot, in accordance with an embodiment. Based on reading (at 402) input data records, various definitions can be made (at 404). For example, the definitions can include value groups defining (column value ranges for respective columns in a visualization screen, and row value ranges for respective rows in the visualization screen). Cells can also be defined to represent the received data records. One or more ordering attributes (to define the order of cells) and a coloring attribute can also be defined.

The value groups (defining rows and columns) of the visualization screen are filled (at 406) with corresponding cells. The cells are then ordered (at 408) from left to right and bottom to top according to the values of the ordering attribute(s). Also, cells are assigned colors (at 410) according to values of the coloring attribute.

All distinct data records are then rendered (at 412) in the visualization screen according to the tasks performed at 406-410.

Thereafter, the procedure repeats based on receiving (at 414) a user interaction or receiving (at 402) further input data records. The user interaction with the visualization screen, can be a selection, a move, or a rubber-banding operation. In response to the user interaction (414), the definitions at 404 can be modified to depict fewer value groups, such as in response to selection of a sub-region in the visualization screen, and/or other actions. Receipt of further input data records can also cause definitions (404) to change, since the further data records can be associated with new values (of the row and column attributes) that may trigger new value groups to be defined, or existing value groups to be modified (value groups may be defined to have more values or less values to enlarge or reduce the respective ranges).

The tasks of FIG. 4 may be provided in the context of information technology (IT) services offered by one organization to another organization. The IT services may be offered as part of an IT services contract, for example.

Figure 5:
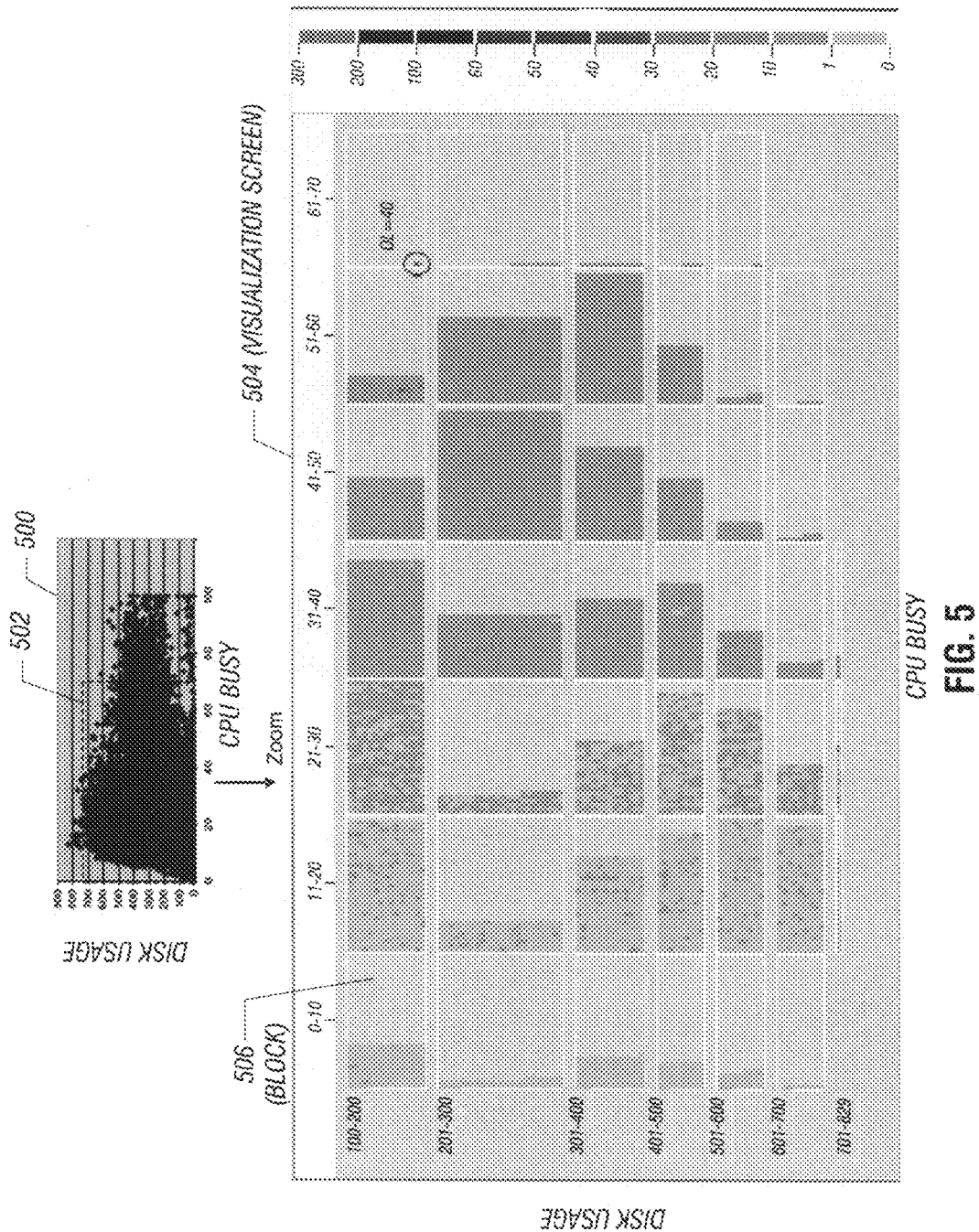
FIG. 5 illustrates how a user can select a portion of a traditional scatter plot for representation in a visualization screen according to an embodiment.

FIG. 5 shows yet another example user interaction that can be made, in this case, with respect to a standard scatter plot 500. The standard scatter plot 500 has a vertical axis corresponding to the attribute Disk usage, and a horizontal axis corresponding to the attribute CPU busy, in one example. As depicted in FIG. 5, a user can select a sub-region 502 of the standard scatter plot 500, which causes a visualization screen 504 to be depicted that shows just the data records of the selected sub-region 502. This is contrasted to FIGS. 1 and 2, where the visualization screen 200 shows all data records that appear in the standard scatter plot of FIG. 1.

The columns of the visualization screen 504 correspond to different value ranges of the CPU busy attribute, and the rows of the visualization screen 504 correspond to different values ranges of the Disk usage attribute. The color assigned to cells within blocks 506 of the visualization screen 504 represent values of Queue length (the coloring attribute). The cells can be ordered by time stamp (the ordering attribute) in the example of FIG. 5.

In the example of FIG. 5, the blocks 506 that are at the intersections of the row corresponding to Disk usage value range 100-200 and the columns corresponding to value ranges 11-20 and 21-30 have the largest number of data records (each of such blocks are almost full). On the other hand, the block at the intersection of the column corresponding to value range 61-70 for CPU busy and the row corresponding to the value range 501-600 for Disk usage has the smallest number of data records are present in the corresponding blocks, as depicted in FIG. 5.

As depicted in FIG. 5, the highest disk usage (row for range 701-829) is associated with relatively low CPU busy values (in the columns corresponding to values between 10-40), a relatively small number of data records are present in the corresponding blocks, as depicted in FIG. 5.

Also, note that there is low disk usage when CPU busy is above 60%. Note that FIG. 5 indicates that CPU busy is related to queue length, but is not related to disk usage.

Figure 6:
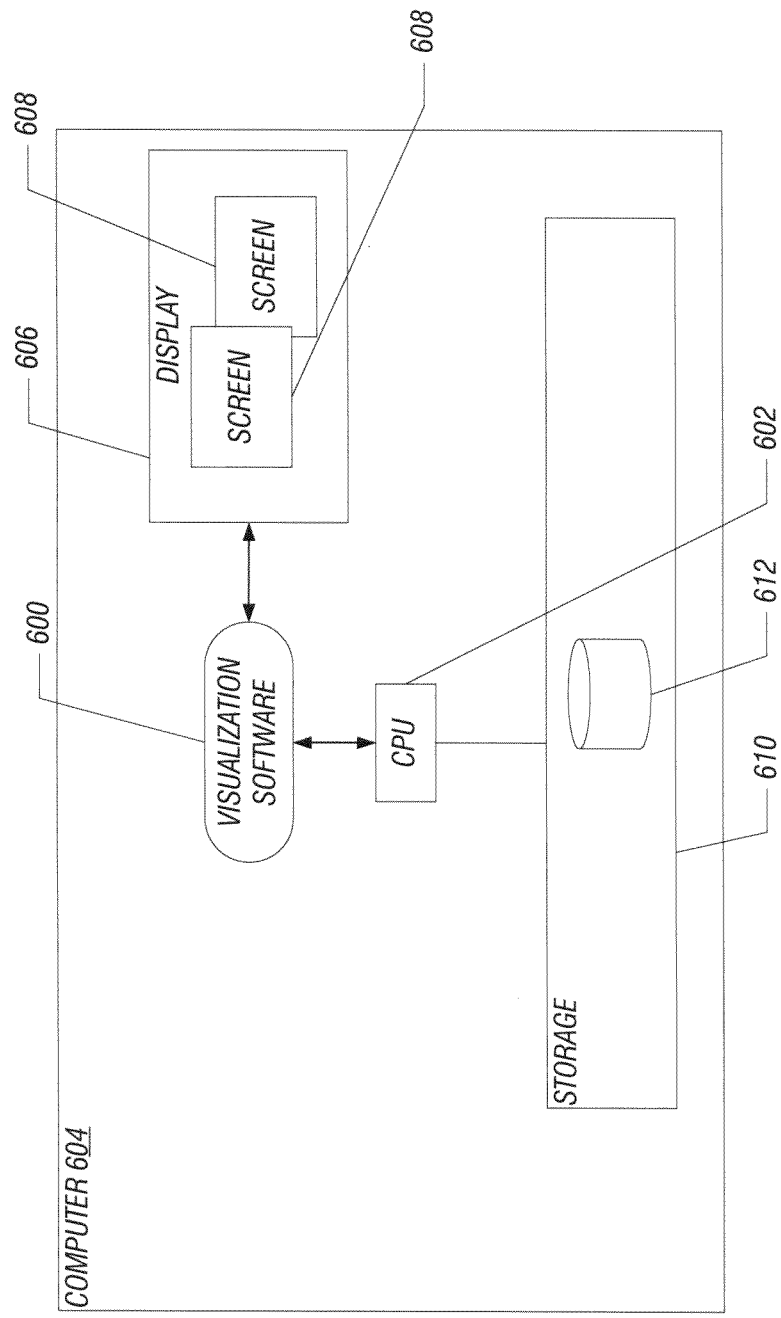
FIG. 6 is a block diagram of a computer including visualization software to provide visualization screens according to some embodiments.

FIG. 6 shows an example computer 604 in which visualization software 600 is executable, in accordance with some embodiments. The visualization software 600 is able to perform the various tasks described above. The visualization software 600 is executed on one or more central processing units (CPUs) 602, which is connected to a storage 610. The storage 610 stores a database 612 that can contain input data records to be processed by the visualization software 600. Alternatively, the input data records can be received in real-time over a network interface.

The computer 604 also includes a display device 606 in which visualization screen 608 (such as the visualization screens depicted in FIGS. 2, 3, and 5) can be presented.

By using the visualization technique or mechanism according to some embodiments, various benefits may be provided. First, overlapping data records that traditionally are present in conventional scatter plots can be avoided in visualization screens according to some embodiments. In this way, the true volume of data records within each value group can be shown to provide a complete view of data value distribution. Also, multiple dimensions can be depicted using various attributes, including attributes to define rows and columns, coloring attributes, and ordering attributes.

Instructions of software described above (including the visualization software 600 of FIG. 6) are loaded for execution on a processor (such as one or more CPUs 602 in FIG. 6). The processor includes microprocessors, microcontrollers, processor modules or subsystems (including one or more microprocessors or microcontrollers), or other control or computing devices. A "processor" can refer to a single component or to plural components.

Data and instructions (of the software) are stored in respective storage devices, which are implemented as one or more computer-readable or computer-usable storage media. The storage media include different forms of memory including semiconductor memory devices such as dynamic or static random access memories (DRAMs or SRAMs), erasable and programmable read-only memories (EPROMs), electrically erasable and programmable read-only memories (EEPROMs) and flash memories; magnetic disks such as fixed, floppy and removable disks; other magnetic media including tape; and optical media such as compact disks (CDs) or digital video disks (DVDs). Note that the instructions of the software discussed above can be provided on one computer-readable or computer-usable storage medium, or alternatively, can be provided on multiple computer-readable or computer-usable storage media distributed in a large system having possibly plural nodes. Such computer-readable or computer-usable storage medium or media is (are) considered to be part of an article (or article of manufacture). An article or article of manufacture can refer to any manufactured single component or multiple components.

In the foregoing description, numerous details are set forth to provide an understanding of the present invention. However, it will be understood by those skilled in the art that the present invention may be practiced without these details. While the invention has been disclosed with respect to a limited number of embodiments, those skilled in the art will appreciate numerous modifications and variations therefrom. It is intended that the appended claims cover such modifications and variations as fall within the true spirit and scope of the invention.

What is claimed is:

1. A method of non-overlapping visualization of data records of a scatter plot, comprising:
   providing, by a computer, rows and columns in a visualization screen containing cells representing respective data records, each of the data records containing a plurality of attributes, wherein the rows correspond to value ranges of a first attribute of the plurality of attributes, and the columns correspond to value ranges of a second attribute of the plurality of attributes, wherein each value range of the value ranges of the first attribute includes plural values of the first attribute, and wherein each value range of the value ranges of the second attribute includes plural values of the second attribute, and wherein blocks are provided at respective intersections of the rows and columns and are identified by visible boundaries, and each of the blocks includes a corresponding arrangement of cells, and the blocks in a first of the rows have a different height than the blocks in a second of the rows;
   automatically generating, by the computer, the value ranges for the rows based on values of the first attribute in the data records;
   automatically generating, by the computer, the value ranges for the columns based on values of the second attribute in the data records; and
   assigning, by the computer, different colors to the cells according to different values of a third attribute of the plurality of attributes.

2. The method of claim 1, further comprising ordering, by the computer, the cells in each of the blocks according to a fourth attribute of the plurality of attributes, the fourth attribute different from the first and second attributes.

3. The method of claim 2, wherein the third attribute is different from the first, second, and fourth attributes.

4. The method of claim 1, wherein the cells are of the same size.

5. The method of claim 1, wherein providing the rows comprises providing the rows where each row does not intrude into a neighboring row.

6. The method of claim 1, wherein providing the columns comprises providing the columns where each column does not intrude into a neighboring column.

7. The method of claim 1, further comprising receiving additional data records, wherein automatically generating the value ranges for the rows and the value ranges for the columns comprises modifying the value ranges for the rows and modifying the value ranges for the columns based on data values of the additional data records.

8. The method of claim 7, wherein modifying the value ranges for the rows comprises adding new value ranges that define new corresponding rows in the visualization screen.

9. The method of claim 1, further comprising:
   receiving an indication of user selection of a sub-region in the visualization screen; and
   creating a second visualization screen in response to the indication, wherein the second visualization screen includes a subset of the data records.

10. The method of claim 9, further comprising automatically generating value ranges for rows and columns in the second visualization screen based on data values of the subset of data records.

11. The method of claim 1, further comprising:
    receiving a user interaction with a given cell of the cells in the visualization screen; and
    in response to the user interaction, displaying a popup box in the visualization screen that contains information relating to a data record represented by the given cell.

12. The method of claim 11, wherein displaying the popup box containing the information comprises displaying the popup box containing information regarding at least one attribute other than or in addition to the first, second, and third attributes.

13. The method of claim 1, further comprising providing information technology services, wherein the providing, the generating, and the assigning tasks are part of the information technology services.

14. The method of claim 1, wherein the rows correspond to the value ranges of just the first attribute that is contained in the data records.

15. A system comprising:
    a non-transitory computer-readable storage medium storing instructions; and
    at least one processor on which the instructions are executable to:
    receive data records, each data record of the data records containing a plurality of attributes;
    define value ranges for corresponding rows and columns for display in a visualization screen, wherein the rows and columns define blocks each containing cells representing respective data records, wherein the rows correspond to value ranges of a first attribute of the plurality of attributes in the data records, and the columns correspond to value ranges of a second attribute of the plurality of attributes in the data records, wherein each value range of the value ranges of the first attribute includes plural values of the first attribute, and wherein each value range of the value ranges of the second attribute includes plural values of the second attribute, and wherein the blocks are identified by visible boundaries, and the blocks of a first of the rows have a different height than the blocks of a second of the rows; and
    assign colors to the cells according to a coloring attribute of the plurality of attributes.

16. The system of claim 15, wherein the blocks are part of a regular array of blocks.

17. The system of claim 15, wherein the rows are each confined between a corresponding first horizontal line and a corresponding second horizontal line, and the columns are each confined between a corresponding first vertical line and a corresponding second vertical line.

18. The system of claim 15, wherein the instructions are executable by the at least one processor to further:
    receive a user interaction with a given cell of the cells in the visualization screen; and
    in response to the user interaction, display a popup box in the visualization screen that contains information relating to a data record represented by the given cell.

19. The system of claim 15, wherein the rows correspond to the value ranges of just the first attribute that is contained in the data records.

20. The system of claim 15, wherein the instructions are executable on the at least one processor to further:
order the cells in each of the blocks according to a fourth attribute of the plurality of attributes, the fourth attribute different from the first and second attribute.

21. An article comprising at least one non-transitory computer-readable storage medium containing instructions that when executed cause a computer to:
provide rows and columns in a visualization screen containing cells representing respective data records of a scatter plot, each of the data records containing a plurality of attributes, wherein the rows correspond to value ranges of a first attribute of the plurality of attributes, and the columns correspond to value ranges of a second attribute of the plurality of attributes, wherein each value range of the value ranges of the first attribute includes plural values of the first attribute, and wherein each value range of the value ranges of the second attribute includes plural values of the second attribute, and wherein blocks are provided at respective intersections of the rows and columns and are identified by visible boundaries, and each of the blocks includes a corresponding arrangement of cells, and the blocks in a first of the rows have a different height than the blocks in a second of the rows;
automatically generate the value ranges for the rows based on values of the first attribute in the data records;
automatically generate the value ranges for the columns based on values of the second attribute in the data records; and
assign different colors to the cells according to different values of a third attribute of the plurality of attributes.

22. The article of claim 21, wherein the instructions when executed cause the computer to further:
order the cells in each of the blocks according to a fourth attribute different from the first and second attributes.

23. The article of claim 21, wherein the instructions when executed cause the computer to further receive additional data records, wherein automatically generating the value ranges for the rows and the value ranges for the columns comprises modifying the value ranges for the rows and the value ranges for the columns based on data values of the additional data records.

24. The article of claim 21, wherein the rows correspond to the value ranges of just the first attribute that is contained in the data records.

* * * * *